United States Patent
Mattes et al.

(10) Patent No.: US 10,687,692 B2
(45) Date of Patent: Jun. 23, 2020

(54) ENDOSCOPE AND METHOD OF SECURING A BUNDLE OF FIBRE-OPTIC LIGHT GUIDES IN A SHAFT OF AN ENDOSCOPE

(71) Applicant: Henke-Sass, Wolf GmbH, Tuttlingen (DE)

(72) Inventors: Andreas Mattes, Duerbheim (DE); Oliver Rehe, Wurmlingen (DE)

(73) Assignee: Henke-Sass, Wolf GmbH, Tuttlingen (DE)

(*) Notice: Subject to any disclaimer, the term of this patent is extended or adjusted under 35 U.S.C. 154(b) by 319 days.

(21) Appl. No.: 15/715,817

(22) Filed: Sep. 26, 2017

(65) Prior Publication Data
US 2018/0084972 A1 Mar. 29, 2018

(30) Foreign Application Priority Data
Sep. 26, 2016 (DE) .................. 10 2016 118 102

(51) Int. Cl.
| A61B 1/00 | (2006.01) |
| A61B 1/06 | (2006.01) |
| A61B 1/07 | (2006.01) |
| G02B 23/24 | (2006.01) |

(52) U.S. Cl.
CPC ........ *A61B 1/00112* (2013.01); *A61B 1/0008* (2013.01); *A61B 1/0011* (2013.01); *A61B 1/0607* (2013.01); *A61B 1/0623* (2013.01); *A61B 1/07* (2013.01); *G02B 23/2469* (2013.01);
(Continued)

(58) Field of Classification Search
CPC combination set(s) only.
See application file for complete search history.

(56) References Cited

U.S. PATENT DOCUMENTS

| 4,850,342 A * | 7/1989 | Hashiguchi ........ A61B 1/00179 600/171 |
| 4,991,565 A * | 2/1991 | Takahashi .......... A61B 1/00142 600/123 |

(Continued)

FOREIGN PATENT DOCUMENTS

| DE | 102004023024 A1 | 12/2005 |
| DE | 102007044663 B3 | 4/2009 |

(Continued)

*Primary Examiner* — John P Leubecker
*Assistant Examiner* — Shankar Raj Ghimire
(74) *Attorney, Agent, or Firm* — Skaar Ulbrich Macari, P.A.

(57) ABSTRACT

An endoscope includes a main unit and a shaft, connected to the main unit, which extends along a longitudinal axis. The shaft includes a jacket tube, an inner tube for receiving an objective lens, and a bundle of fibre-optic light guides. The inner tube includes, at a distal end, an inner tube head which includes a first bearing section and a second bearing section, which is connected to the first bearing section by a connecting element. The first bearing section includes a first bearing surface, against which the bundle of fibre-optic light guides abuts, and the second bearing section includes a second bearing surface, against which the bundle of fibre-optic light guides abuts, wherein, to align the bundle of fibre-optic light guides at the distal end, an area of the first bearing surface and/or an area of the second bearing surface run non-parallel to the longitudinal axis.

12 Claims, 5 Drawing Sheets

(52) U.S. Cl.
CPC ........ *G02B 23/2476* (2013.01); *G02B 23/243* (2013.01)

(56) References Cited

U.S. PATENT DOCUMENTS

| | | | | |
|---|---|---|---|---|
| 5,051,824 | A * | 9/1991 | Nishigaki | A61B 1/00179 348/68 |
| 5,159,920 | A * | 11/1992 | Condon | A61B 1/042 600/121 |
| 5,169,568 | A * | 12/1992 | Ainger, III | A61B 1/015 264/1.25 |
| 5,554,100 | A * | 9/1996 | Leiner | A61B 1/00179 385/117 |
| 5,573,493 | A * | 11/1996 | Sauer | A61B 1/00101 600/121 |
| 6,110,103 | A * | 8/2000 | Donofrio | A61B 1/126 600/114 |
| 10,357,149 | B2 * | 7/2019 | Hoyle | A61B 1/128 |
| 2005/0250992 | A1 * | 11/2005 | Scherr | A61B 1/07 600/182 |
| 2007/0083081 | A1 * | 4/2007 | Schlagenhauf | A61B 1/00135 600/104 |
| 2011/0208001 | A1 * | 8/2011 | Haeckl | A61B 1/00071 600/125 |
| 2012/0033911 | A1 * | 2/2012 | Wang | A61B 5/0062 385/11 |
| 2012/0271113 | A1 * | 10/2012 | Lei | A61B 1/00167 600/175 |
| 2012/0289858 | A1 * | 11/2012 | Ouyang | A61B 10/0275 600/562 |
| 2015/0094539 | A1 * | 4/2015 | Eisenkolb | A61B 1/0011 600/182 |
| 2017/0261742 | A1 * | 9/2017 | Wieters | A61B 1/0008 |
| 2017/0319186 | A1 * | 11/2017 | Van Der Zaag | A61B 5/0071 |

FOREIGN PATENT DOCUMENTS

| | | |
|---|---|---|
| DE | 102013112282 A1 | 1/2014 |
| DE | 102014111069 A1 | 2/2016 |
| JP | 2012141418 A | 7/2012 |

* cited by examiner

ENDOSCOPE AND METHOD OF SECURING A BUNDLE OF FIBRE-OPTIC LIGHT GUIDES IN A SHAFT OF AN ENDOSCOPE

PRIORITY

This application claims the benefit of German Patent Application No. 102016118102.1, filed on Sep. 26, 2016, which is hereby incorporated herein by reference in its entirety.

FIELD

The present invention relates generally to an endoscope with a main unit and a shaft, connected to the main unit, which extends along a longitudinal axis, wherein the shaft comprises a jacket tube, an inner tube arranged in the jacket tube for receiving an objective lens, and bundles of fibre-optic light guides which run along the longitudinal axis in the shaft between the jacket tube and the inner tube. The invention furthermore relates generally to a method of securing a bundle of fibre-optic light guides in a shaft of an endoscope by providing a jacket tube which extends along a longitudinal axis, and by providing an inner tube.

BACKGROUND

Endoscopes are used, e.g., in order to visually examine body cavities that are not visible from the outside. For this, endoscopes known from the state of the art comprise a shaft and a main unit. An objective lens is provided at a distal end of the shaft, i.e. an end of the shaft facing away from the main unit, and an eyepiece is provided on the main unit. The distal end of the shaft is inserted into the body cavity and the inside of the body cavity is imaged via the objective lens and the eyepiece. In order also to observe the body cavity laterally to a longitudinal axis of the shaft, in known endoscopes it is provided to arrange an optical axis of the objective lens diagonally to the longitudinal axis of the shaft; the optical axis of the objective lens and the longitudinal axis of the shaft therefore form an angle.

In endoscopes it is furthermore known to guide fibre-optic light guides through the shaft, which can be used to illuminate the inside of the body. In order to align the fibre-optic light guides at the distal end of the shaft with respect to the orientation of the objective lens, it is known to insert a wedge at the distal end of the shaft between the fibre-optic light guides and a tube of the shaft during assembly of the endoscope, with the result that the fibre-optic light guides are aligned approximately parallel to the optical axis at the distal end.

SUMMARY

An object of certain embodiments of the invention is to provide an endoscope and a method of securing a bundle of fibre-optic light guides in a shaft of an endoscope, which can be produced and, respectively, carried out particularly reliably and quickly.

The disclosure includes both endoscope devices and methods or forming an endoscope.

The disclosure includes an endoscope which may comprise a main unit and a shaft, connected to the main unit, which extends along a longitudinal axis. The shaft comprises a jacket tube, an inner tube arranged in the jacket tube for receiving an objective lens, and a bundle of fibre-optic light guides which run along the longitudinal axis in the shaft between the jacket tube and the inner tube. At a distal end facing away from the main unit the inner tube comprises an inner tube head, which comprises a first bearing section and a second bearing section, which is connected to the first bearing section by a connecting element. The first bearing section comprises a first bearing surface, against which the bundle of fibre-optic light guides abuts, and the second bearing section comprises a second bearing surface, against which the bundle of fibre-optic light guides abuts and which lies opposite the first bearing surface at least in areas. To align the bundle of fibre-optic light guides off the longitudinal axis at the distal end, an area of the first bearing surface and/or an area of the second bearing surface run non-parallel to the longitudinal axis.

An advantage of the endoscope is that the arrangement of the bundle of fibre-optic light guides at the distal end is achieved particularly simply and reliably in that the bundle of fibre-optic light guides is arranged between the areas of the first and second bearing surfaces which lie opposite each other. Because the corresponding areas of the first and second bearing surfaces lie opposite each other, a temporary securing of the position of the fibre-optic light guides relative to each other can be achieved. The insertion of the bundle of fibre-optic light guides, together with the inner tube, into the jacket tube of the shaft can thereby be facilitated, as the shifting of the fibre-optic light guides relative to each other is made difficult. At the same time, the bundle of fibre-optic light guides is aligned at the distal end with respect to the orientation of the objective lens, as the first bearing surface and/or the second bearing surface are inclined relative to the longitudinal axis. This means that, through the provision of the first bearing section and the second bearing section, the insertion of the bundle of fibre-optic light guides can be simplified and at the same time the alignment of the bundle of fibre-optic light guides is achieved. In particular, the temporary arrangement of the bundle of fibre-optic light guides between the first bearing surface and the second bearing surface makes a precise alignment of the bundle of fibre-optic light guides at the distal end possible. The subsequent insertion of a wedge, as is known from the state of the art, often led to shifts in the bundle of fibre-optic light guides, with the result that these have to be rearranged, during or after the insertion of the wedge. This means that in the state of the art the bundle of fibre-optic light guides was arranged for insertion into the jacket tube, then the wedge was introduced and, during or after that, the bundle of fibre-optic light guides often has to be rearranged. In the endoscope according to the invention the fibre-optic light guides only have to be positioned once, wherein the arrangement can be significantly simplified through the provision of two bearing surfaces which lie opposite each other, as the bundle of fibre-optic light guides can be clamped between the first bearing surface and the second bearing surface.

The endoscope can be preferably used for the examination of a body cavity and, optionally apart from the distal end, has a structure such as is known from the state of the art. The main unit can be connected to the shaft by means of joining, in particular welding, brazing or gluing. An eyepiece which, together with an objective lens provided at the distal end as well as optionally with lenses arranged in the shaft and/or in the main unit, forms an imaging optical system by means of which the inside of a body cavity can be imaged can be provided on the main unit. The eyepiece is provided at a proximal end of the endoscope.

Furthermore, on the main unit, an optical connection can be provided from which the bundle of fibre-optic light guides extends to the distal end and by means of which radiation can be coupled into the bundle of fibre-optic light guides. For this, for example, the optical connection is connected to a light source, such as for example an LED light source or a halogen light source.

The shaft extends along the longitudinal axis, wherein the inner tube, the bundle of fibre-optic light guides and the jacket tube also extend along the longitudinal axis; in particular this does not apply to an area at the distal end of the endoscope. The jacket tube represents the outer surface of the shaft and the bundle of fibre-optic light guides and the inner tube are arranged in its internal space. Lenses, rod lenses or other optical elements of the imaging optical system can be arranged in the inner tube. The fibre-optic light guide can comprise an optical fibre made of a polymer or similar materials. The fibre-optic light guide can be formed such as is known from the state of the art. The bundle comprises in particular two or more fibre-optic light guides which end at the distal end and there emit the light coupled in at the optical connection, with the result that a plurality of light sources form at the distal end. The jacket tube and/or the inner tube as well as the inner tube head can be produced from a metallic material, in particular stainless steel.

The inner tube head can be formed in one piece with the inner tube, but it is preferred for the inner tube and the inner tube head to be formed in two pieces. The inner tube head is optionally connected to the inner tube by means of a joining process, such as for example brazing, gluing or welding. The inner tube head itself can be formed as a one-piece unit. The inner tube head is optionally used to secure the objective lens and contributes to the arrangement of the bundle of fibre-optic light guides. In order to secure the bundle of fibre-optic light guides at the distal end, the inner tube head and the bundle of fibre-optic light guides, as well as optionally the jacket tube, can be connected with adhesive.

The inner tube, preferably the inner tube head, further preferably the first bearing section, optionally comprises an objective lens receiver in which the objective lens is arranged. For example, the objective lens receiver has a thread by means of which the objective lens can be screwed in. An optical axis of the objective lens can extend from the objective lens in the direction of the distal end to the object to be imaged in front of the distal end of the objective lens. The optical axis is in particular arranged in such a way that it forms an angle with the longitudinal axis, whereby an endoscope with a viewing angle not equal to 0° relative to the longitudinal axis can be provided. The viewing angle can lie in a range of from 5° to 80°, preferably from 15° to 70° and further preferably from 25° to 60°. Values of from 30° to 45° or 50° are also possible. An opening angle of an imageable area can be, e.g., ±10°, ±15° or ±20° relative to the optical axis. The viewing angle and the opening angle define the field of view of the endoscope. The optical axis of the objective lens is in particular perpendicular to an end plane of the shaft at the distal end. This end plane can be inclined, as in endoscopes known from the state of the art, relative to a plane perpendicular to the longitudinal axis. The end plane is optionally formed by the first bearing section, the second bearing section, the connecting element, the bundle of fibre-optic light guides, the objective lens and/or the jacket tube. In particular, these elements are arranged entirely flush with the end plane.

In top view onto the distal end, the first bearing section comprises an inner surface, which is optionally designed as an objective lens receiver, and an outer surface. A portion of the outer surface forms the first bearing surface, wherein an area of the first bearing surface is arranged spaced apart from and lying opposite the second bearing surface. In order to durably define the mutual arrangement of the two bearing surfaces, with the result that a better arrangement of the bundle of fibre-optic light guides is possible, the first bearing section and the second bearing section are connected to each other by the connecting element. The connecting element can assume any form, as long as a durable and stable connection between the first bearing section and the second bearing section is made possible. The connecting element can be arranged flush with the end plane; however, it is also possible for the connecting element to be spaced apart from the end plane, for example the connecting element is arranged inside the shaft.

In this way, the bundle of fibre-optic light guides is delimited over a large surface area by the first bearing surface and the second bearing surface, with the result that the bundle of fibre-optic light guides can be inserted particularly simply into the jacket tube. For example, in top view onto the distal end, the bundle of fibre-optic light guides is only delimited by the first bearing surface, the connecting element, the second bearing surface and the jacket tube. The proportion of the jacket tube compared with the remaining elements is preferably small; it is preferred for the bundle of fibre-optic light guides to be delimited at the distal end only by the connecting element, the first bearing surface and the second bearing surface. Depending on the number of fibre-optic light guides, all or a partial quantity of the fibre-optic light guides abut against the first and/or the second bearing surface. For example, if many thin fibre-optic light guides are provided, only the outer fibre-optic light guides of the bundle in each case abut against the bearing surfaces.

Areas of the first bearing surface and/or the second bearing surface are arranged non-parallel to the longitudinal axis, i.e. these areas of the first and/or second bearing surface form an angle with the longitudinal axis. This angle is determined in particular in a plane perpendicular to the corresponding areas of the first and/or second bearing surface. Because the bundle of fibre-optic light guides abuts against the first bearing surface and the second bearing surface, at least some of the fibre-optic light guides are deflected out of their course along the longitudinal axis, with the result that the direction of the principal illumination of the deflected portion of the fibre-optic light guides is non-parallel to the longitudinal axis.

In order to facilitate a sealing of the distal end of the shaft and to simplify the arrangement of the bundle of fibre-optic light guides at the distal end, it is preferred for the first bearing section and/or the second bearing section to abut against an inner surface of the jacket tube. The first bearing section and/or the second bearing section, in the circumferential direction of the jacket tube, preferably abut flush against the latter. In particular, the portion of the outer surface of the first bearing section that is not used as first bearing surface abuts against the inner surface of the jacket tube. The first bearing section can be formed annular. The second bearing section can be formed crescent-shaped. In top view onto the distal end, the second bearing section optionally only comprises the second bearing surface and a surface by means of which it abuts against the inner surface of the jacket tube.

In addition, the development of the endoscope according to which the first bearing section and the second bearing section abut against an inner surface of the jacket tube allows a particularly precise arrangement of the bundle of fibre-optic light guides as, through the abutment of the first and second bearing sections, the bundle of fibre-optic light guides is predetermined with respect to the alignment relative to the longitudinal axis. For this, it is preferred for the surfaces at which the first bearing section and the second bearing section abut against the inner tube of the jacket tube to lie opposite each other, with the result that only the orientation along the circumferential direction has to be defined.

In order to optimize the illumination provided by the endoscope, it is preferred for the endoscope to comprise an objective lens with an optical axis which forms an angle with the longitudinal axis which is equal to an angle which the longitudinal axis forms with the area of the first bearing surface and/or the area of the second bearing surface. This means that the optical axis runs in a plane parallel to the inclined area of the first bearing surface and/or the second bearing surface. It is thereby achieved that the individual fibre-optic light guides which abut against the inclined area of the first and/or second bearing surface run parallel to the optical axis. The direction of the illumination is thereby parallel to the optical axis of the objective lens, with the result that the area observed using the objective lens is illuminated particularly well.

In order to provide a homogeneous illumination of the object to be observed with the endoscope, it is preferred for partial areas of the first bearing surface and/or of the second bearing surface to be inclined to different extents relative to the longitudinal axis, wherein the angle preferably increases in the circumferential direction. For example, the first bearing surface and/or the second bearing surface comprise two or more partial areas which are inclined to different extents relative to the longitudinal axis. Optionally, only the first bearing surface comprises partial areas which are inclined to different extents. For example, a partial area of the first bearing surface which is not arranged lying opposite the second bearing surface is inclined to a greater extent relative to the longitudinal axis than the partial area which lies opposite the second bearing surface. The first bearing surface and/or second bearing surface can change the inclination relative to the longitudinal axis gradually, in particular along the circumferential direction of the shaft.

In an example embodiment of the endoscope, two partial areas of the first bearing surface are provided which are inclined to a greater extent relative to the area of the first bearing surface which lies opposite the second bearing surface and these are optionally arranged on opposite sides of the objective lens. These opposite sides are preferably arranged at one level of the optical axis, wherein the area of the first bearing surface which lies opposite the second bearing surface is arranged higher, thus further removed from the optical axis in a height direction. Because of the greater inclination, it can be achieved that the fibre-optic light guides not only provide an illumination around the objective lens, but also illuminate other areas. A distribution of the direction of the illumination can thus be achieved for the individual fibre-optic light guides, whereby the object which is to be viewed with the endoscope can be illuminated more homogeneously.

The areas of the first bearing surface and of the second bearing surface which lie opposite each other can be inclined relative to the longitudinal axis such that the distance between them decreases in the direction towards the distal end.

Furthermore a space delimited by the first and second bearing sections can become smaller towards the distal end. In other words, the delimited space expands towards the proximal end of the endoscope.

In a further embodiment, it is preferred for the connecting element to be formed as a web, wherein the first bearing surface and/or the second bearing surface protrude from the web. For example, the first bearing surface, the connecting element and the second bearing surface, in top view onto the distal end, form a T shape, a double T shape or a C shape. It is preferred for first bearing section, the connecting element and the second bearing section, in top view onto the distal end, to form a double T shape. The first bearing section and/or the second bearing section can have free ends. In particular both bearing sections (or both bearing surfaces), together with the connecting element, in top view onto the distal end, can form one or more laterally open receiver areas for the fibre-optic light guides. The web represents a particularly simple embodiment of a connecting element. It is also possible for the connecting element to comprise two or more webs.

In order to further simplify the arrangement of the light bundles, it is preferred for the fibre-optic light guides to be separated by the connecting element into at least two partial bundles at the distal end. In this way a partial quantity of the fibre-optic light guides can be aligned separately, whereby the number of fibre-optic light guides to be arranged in each case is reduced. This simplifies the arrangement, wherein at the same time it is furthermore possible to arrange the entire number of fibre-optic light guides, but in intermediate steps in each case. This separation is achieved particularly well when the connecting element, in particular the web, is arranged in the centre, with the result that two chambers form, wherein each chamber is delimited by the connecting element, the first bearing surface, the second bearing surface as well as optionally by the inside of the jacket tube.

A particularly homogeneous illumination of the object can be achieved by the inner tube head, in top view onto the distal end, being symmetrical, optionally relative to an axis of symmetry or a plane of symmetry running through the connecting element, in which the connecting element and the longitudinal axis lie. In particular the web forms the axis of symmetry. This means that the fibre-optic light guides are arranged identically on each side of the axis of symmetry, with the result that the object is illuminated symmetrically, preferably relative to the axis of symmetry. In particular, for this, the first bearing surface and the second bearing surface are formed identically on each side of the axis of symmetry. The optical axis of the objective lens preferably runs in the plane of symmetry. In this way, the illumination is aligned particularly well onto the objective lens.

In addition, the invention furthermore develops a method of securing a bundle of fibre-optic light guides in a shaft of an endoscope, which comprises the following steps: providing a jacket tube which extends along a longitudinal axis; providing an inner tube, wherein at the distal end the inner tube comprises an inner tube head with a first bearing section and a second bearing section, which is connected to the first bearing section by a connecting element, wherein the first bearing section comprises a first bearing surface and the second bearing section comprises a second bearing surface, which lies opposite the first bearing surface at least in areas, and wherein an area of the first bearing surface and/or an area of the second bearing surface run non-parallel to the longitudinal axis; aligning the bundle of fibre-optic light guides off the longitudinal axis at the distal end by placing the bundle of fibre-optic light guides against the first bearing surface and/or the second bearing surface; inserting the bundle of fibre-optic light guides and the inner tube into the jacket tube, securing the bundle of fibre-optic light guides on the inner tube head and/or the jacket tube. Optionally, the distal end can be ground.

The inner tube head can comprise a protrusion which protrudes in the direction of the longitudinal axis as well as perpendicularly to the longitudinal axis and the insertion of the bundle of fibre-optic light guides with the inner tube into the jacket tube can be carried out such that the protrusion protrudes in the direction of the longitudinal axis as well as perpendicularly to the longitudinal axis and that the protrusion is arranged in a recess at the distal end of the jacket tube. The recess can extend along the longitudinal axis and/or extend up to the distal end, with the result that it is open towards the distal end.

An advantage of providing the protrusion and the recess is that the inner tube head can be positioned particularly simply in the circumferential direction. The alignment in the circumferential direction is determined by the protrusion and the recess. If the first bearing section and the second bearing section furthermore abut against the inner surface of the jacket tube, as was described previously, the positioning of the inner tube head in the jacket tube is clearly defined, with the result that errors can be avoided during the production of the endoscope.

The protrusion can be arranged on the first bearing section or on the second bearing section. The protrusion is preferably formed in one piece with the inner tube head. The protrusion protrudes perpendicularly to the longitudinal axis, in particular only in the area in which it protrudes in the direction of the longitudinal axis; optionally the protrusion protrudes from the inner tube head in the direction of the optical axis of the objective lens. If the end plane is formed by the first bearing section and/or the second bearing section, the protrusion juts out of the end plane. Because the protrusion protrudes perpendicularly to the longitudinal axis, i.e. in the radial direction of the jacket tube, it can be inserted into the recess of the jacket tube in order to secure the inner tube head in the circumferential direction. The recess is provided at the distal end of the jacket tube head. The protrusion preferably fits flush into the recess.

The bundle of fibre-optic light guides is secured in particular by the application of adhesive, as was described previously. In particular the considerations, preferred embodiments and advantages given in connection with the endoscope apply analogously to the method.

In order to seal the distal end of the shaft reliably, it is preferred for the distal end to be ground in such a way that the extent of the protrusion is removed in the direction of the longitudinal axis. Because the protrusion preferably also protrudes perpendicularly to the longitudinal axis only in the area in which it protrudes in the direction of the longitudinal axis, the protrusion is completely ground off by the grinding of the protrusion in the direction of the longitudinal axis. At the same time the recess is also ground away, as the protrusion extends into the recess. After the grinding, the protrusion and the recess have thus vanished, with the result that the surface area which has to be sealed is reduced. In particular the distal end is ground parallel to the desired end plane.

The disclosure further includes a method of securing at least one fibre-optic light guide in a shaft of an endoscope, comprising the steps: providing a jacket tube which extends along a longitudinal axis and comprises a recess at a distal end; providing an inner tube, wherein the inner tube comprises, at a distal end, an inner tube head which comprises a protrusion; inserting the inner tube into the jacket tube in such a way that the protrusion protrudes in the direction of the longitudinal axis as well as perpendicularly to the longitudinal axis and that the protrusion is arranged in a recess at the distal end of the jacket tube; inserting a bundle of fibre-optic light guides into the jacket tube; securing the bundle of fibre-optic light guides on the inner tube head and the jacket tube; and grinding the distal end.

The previously given considerations, preferred developments and advantages apply analogously to this method.

It is understood that the features named above and those yet to be explained below can be used not only in the stated combinations but also in other combinations or alone, without departing from the scope of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

The invention is explained in yet more detail below with the aid of embodiment examples with reference to the attached drawings, which also disclose features essential to the invention. These embodiment examples merely serve the purpose of illustration and are not to be interpreted as limiting. For example, a description of an embodiment example with a plurality of elements or components is not to be interpreted to the effect that all of these elements or components are necessary for the implementation. Rather, other embodiment examples can also contain alternative elements and components, fewer elements or components or additional elements or components. Elements or components of different embodiment examples can be combined with each other, unless otherwise indicated. Modifications and alterations which are described for one of the embodiment examples can also be applicable to other embodiment examples. To avoid repetitions, the same or corresponding elements are given the same reference numbers in different figures and are not explained repeatedly.

Figure 1:
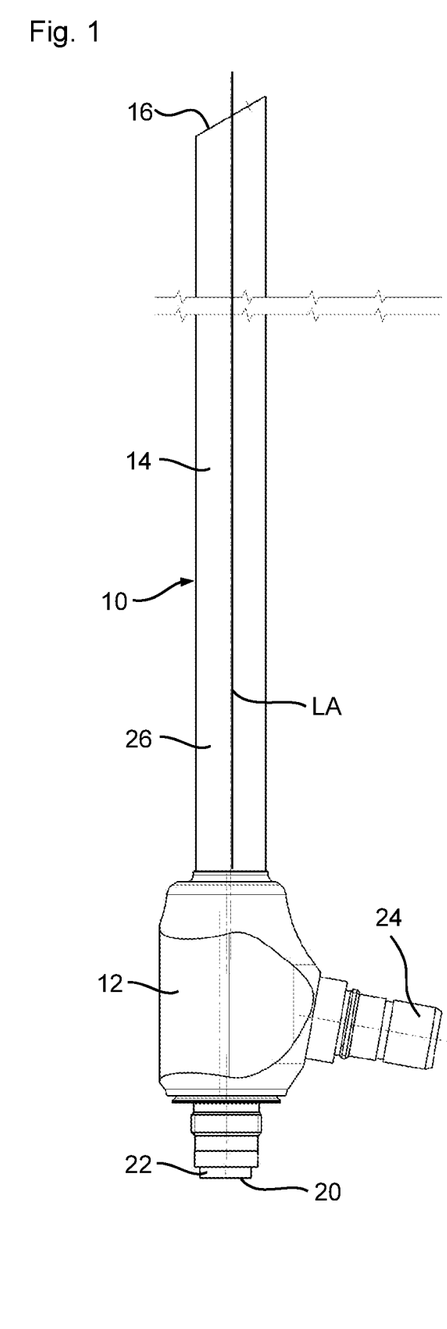
FIG. 1 is a side view of an endoscope.
Figure 2:
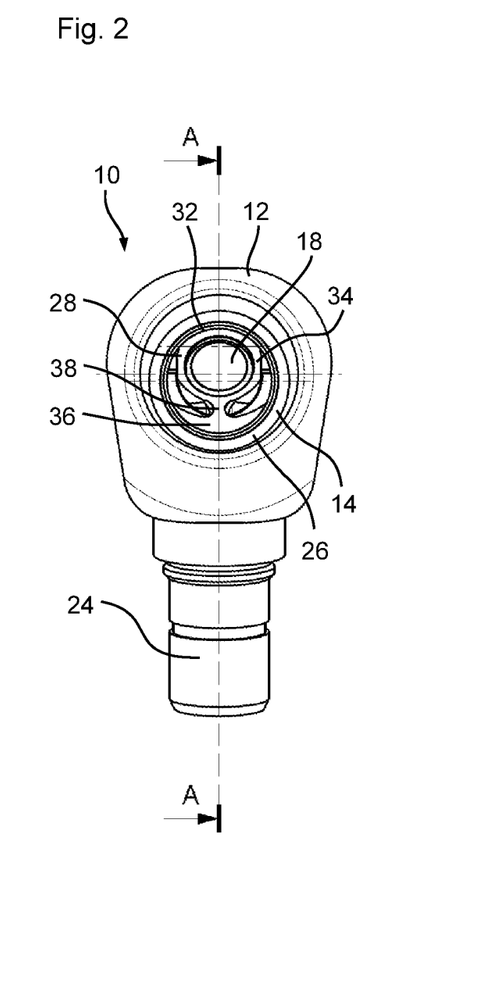
FIG. 2 is a top view onto a distal end of the endoscope according to FIG. 1.

An endoscope 10 comprises a main unit 12 and a shaft 14. The main unit 12 is connected to the shaft 14, for example the connection is realized by means of joining, such as brazing or welding. The shaft 14 extends along a longitudinal axis LA. The endoscope 10 comprises a distal end 16, at which an objective lens 18 is provided, as can be seen in particular in FIGS. 2 and 3. An eyepiece 22 is provided at a proximal end 20 of the endoscope 10. With the aid of the objective lens 18 and the eyepiece 22 and possibly further optical elements that are not represented, an object which is arranged in front of the distal end can be imaged through the endoscope 10. Thus, the distal end 16 of the endoscope 10 can be inserted for example into a body cavity, with the result that the inside of the body cavity can be viewed by means of the eyepiece 22.

Figure 6A:
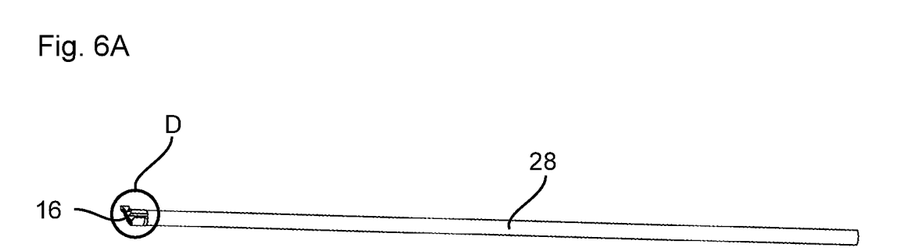
FIG. 6A is a side view of an inner tube of the endoscope of FIG. 1.
Figures 6B, 7A:
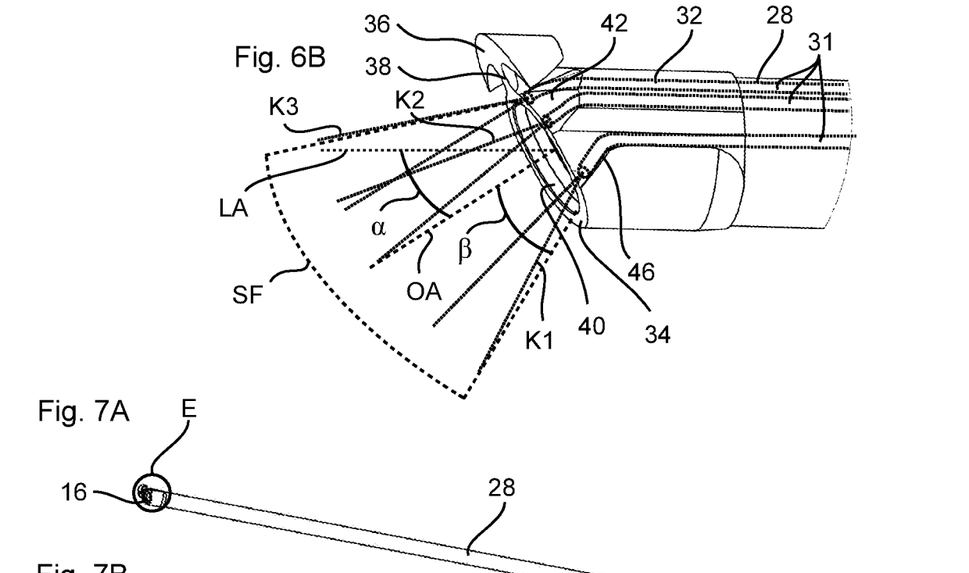
FIG. 6B is an enlarged representation of detail D of FIG. 6A.
FIG. 7A is a perspective view of the inner tube of FIG. 6 diagonally from below.
Figure 7B:
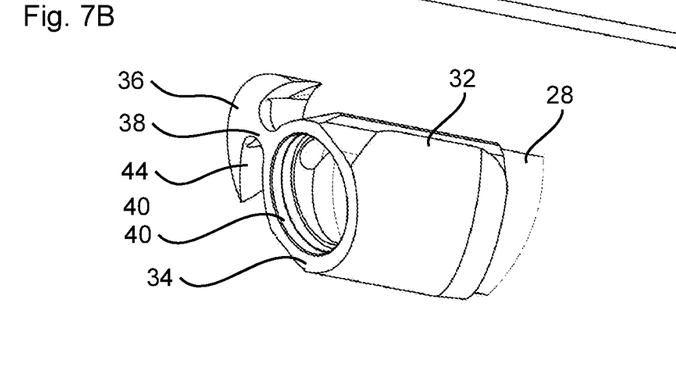
FIG. 7B is an enlarged representation of detail E of FIG. 7A.
Figures 8A, 8B:
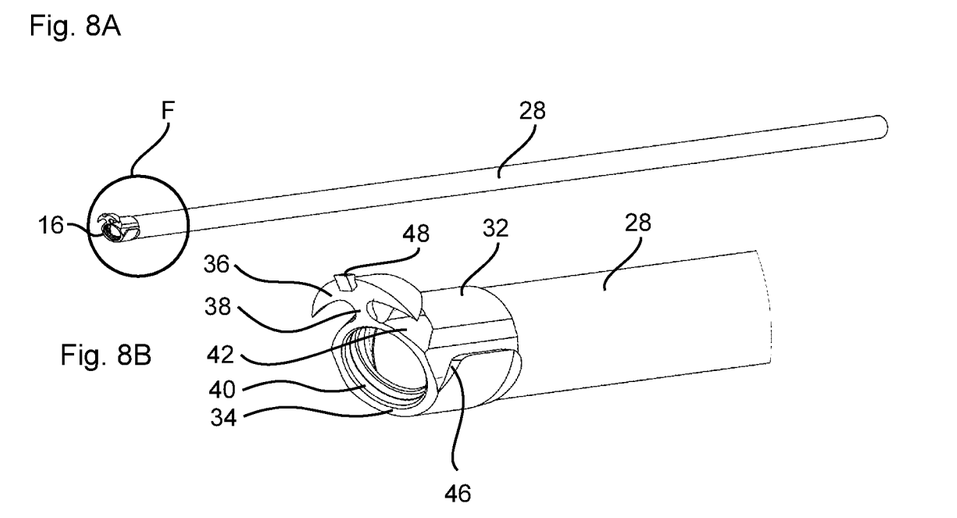
FIG. 8A is the inner tube according to FIGS. 6 and 7, before being built into the endoscope.
FIG. 8B is an enlarged representation of detail F of FIG. 8A.
Figures 9A, 9B:
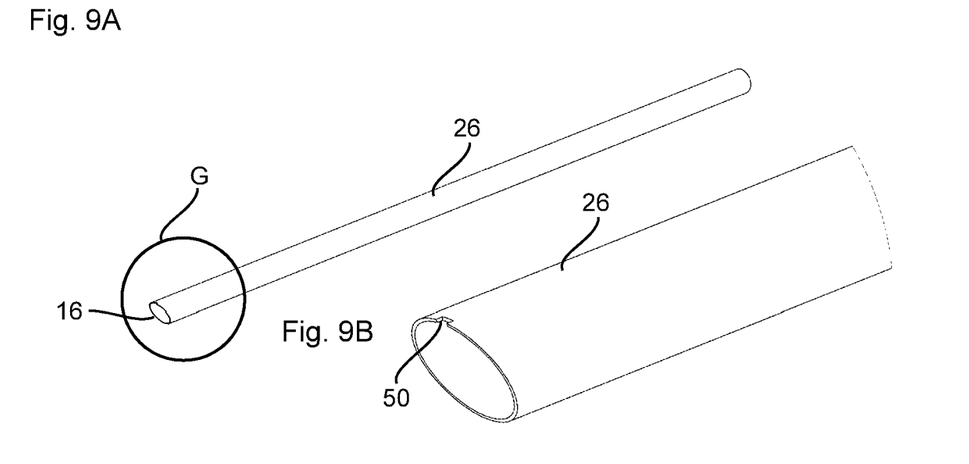
FIG. 9A is a perspective representation of a jacket tube of the endoscope represented in FIG. 1 before being built into the endoscope.
FIG. 9B is an enlarged representation of detail G of FIG. 9A.

An optical connection 24 for a light source (not shown) is provided on the main unit 12. From the optical connection 24, a bundle of fibre-optic light guides 31 extends through the main unit 12 and the shaft 14 to the distal end 16. To simplify the representations, the fibre-optic light guides 31 are only drawn in schematically in FIG. 6B. Although three fibre-optic light guides 31 are represented in FIG. 6B, as a rule the bundle of fibre-optic light guides 31 comprises very many more fibre-optic light guides 31 (e.g. a few hundred or a few thousand). The fibre-optic light guides 31 serve to guide the light from the light source connected to the optical connection 24 to the distal end 16 and to emit it there for the illumination of the object to be observed.

Figure 3:
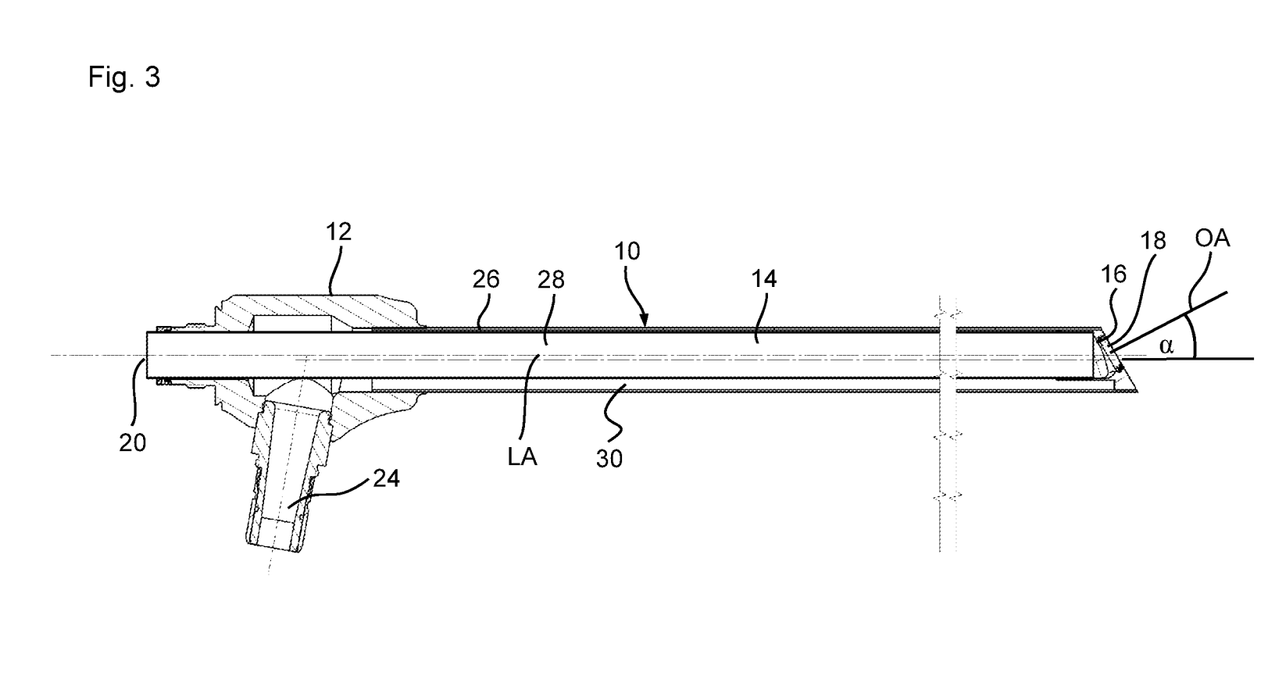
FIG. 3 is a cross-sectional view of the endoscope along the line A-A of FIG. 2.
Figure 4A:
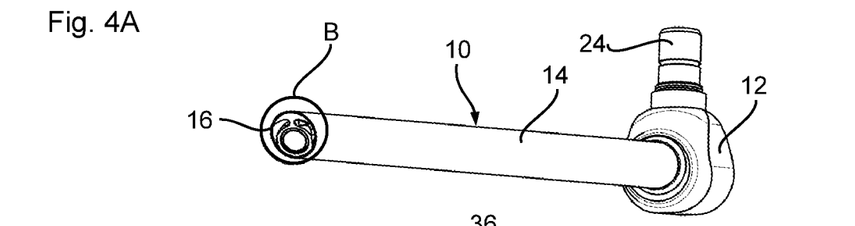
FIG. 4A is a perspective view of the endoscope of FIG. 1 from the side.
Figure 4B:
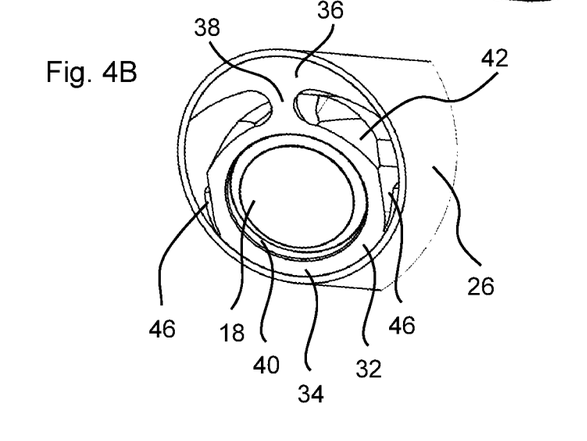
FIG. 4B is an enlarged representation of detail B of FIG. 4A.
Figures 5A, 5B:
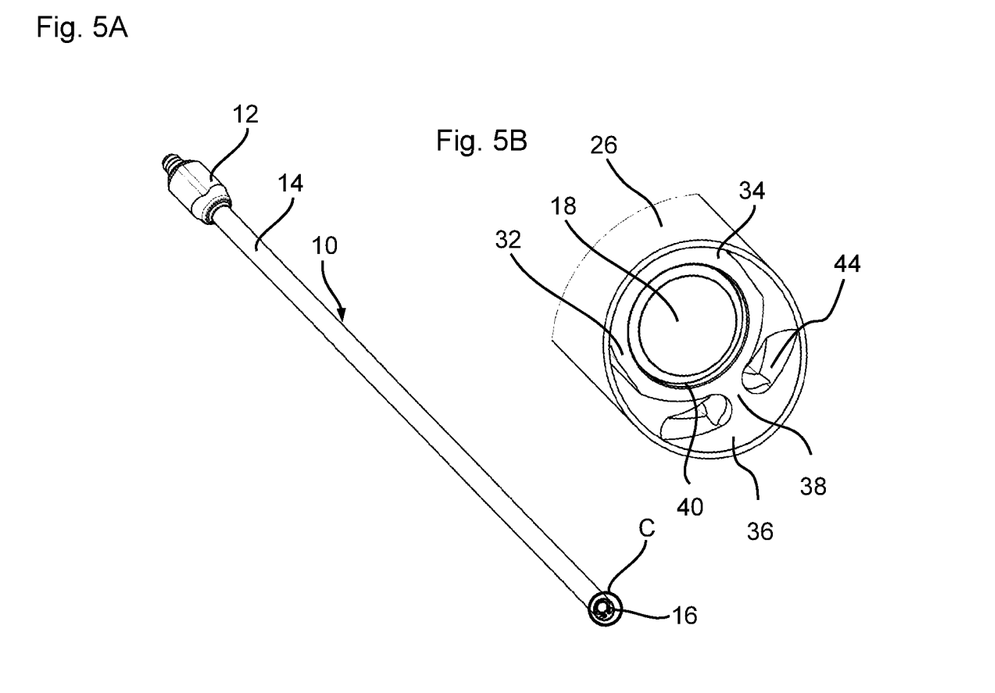
FIG. 5A is a perspective view of the endoscope of FIG. 1 from above.
FIG. 5B is an enlarged representation of detail C of FIG. 5A.

As can be seen in particular in FIG. 3, the shaft 14 comprises a jacket tube 26 and an inner tube 28, both of which run along the longitudinal axis LA. The inner tube 28 is arranged in the jacket tube 26. The inner tube 28 has an external tube diameter which is smaller than an internal tube diameter of the jacket tube 26. A cavity 30 in which the bundle of fibre-optic light guides 31 can be arranged thereby results. The bundle of fibre-optic light guides 31 extends from the optical connection 24, through the shaft 14, along the longitudinal axis LA, to the distal end 16. There, the fibre-optic light guides 31 are deflected off the longitudinal axis LA, with the result that they illuminate the object (see FIG. 6B). Rod lenses, not shown, which provide an optical connection between the objective lens 18 and the eyepiece 22 can be arranged in the inner tube 28.

The inner tube 28 comprises an inner tube head 32 at the distal end 16, i.e. an end facing away from the main unit 12. The objective lens 18 is secured by the inner tube 28, in particular by the inner tube head 32. As can be seen in particular in FIGS. 4-7, the inner tube head 32 comprises a first bearing section 34, a second bearing section 36 and a connecting element 38. The inner tube head 32 can be formed in one piece with the inner tube 28. However, it is preferred for the inner tube head 32 to be durably connected to the inner tube 28 with the aid of a joining method, for example by means of brazing, gluing or welding. The jacket tube 26, the inner tube 28 and/or the inner tube head 32 are produced from a metallic material, for example stainless steel.

The first bearing section 34 comprises an objective lens receiver 40 and a first bearing surface 42. The objective lens receiver 40 can be formed, in top view, as a circular opening, in which the objective lens 18 can be secured. The objective lens receiver 40 is arranged in such a way that an optical axis OA of the objective lens 18 is inclined relative to the longitudinal axis LA and forms an angle $\alpha$ (FIG. 3; FIG. 6B). In this way, it is possible for the object to be viewed laterally to the longitudinal axis LA with the endoscope 10, i.e. for objects to be viewed not only along the longitudinal axis LA by means of the endoscope 10. The optical axis OA thus defines a viewing angle. An opening angle $\beta$ of the objective lens 18 which, together with the viewing angle, defines a field of view SF of the endoscope 10 can be for example ±5°, ±10°, ±15°, ±20°, ±25°, ±30°, ±35° or ±37.5° about the optical axis OA. The field of view SF is represented by way of example in FIG. 6B. The first bearing surface 42 is located on an outer surface of the first bearing section 34. A further section of the outer surface of the first bearing section 34 abuts against the jacket tube 26, preferably flush along its circumferential direction. The bundle of fibre-optic light guides 31, which, as mentioned, are not represented in the figures, abuts against the first bearing surface 42.

The second bearing section 36 likewise abuts, preferably flush in the circumferential direction of the jacket tube 26, against the latter. In addition, the second bearing section 36 comprises a second bearing surface 44, against which the bundle of fibre-optic light guides 31 likewise abuts. The first bearing surface 42 and the second bearing surface 44 are arranged non-parallel at least in areas relative to the longitudinal axis LA. This means that areas of the first bearing surface 42 and/or of the second bearing surface 44 form an angle with the longitudinal axis LA. These areas of the first bearing surface 42 and of the second bearing surface 44 lie opposite each other. The first bearing surface 42 and/or the second bearing surface 44 preferably run parallel to the optical axis OA of the objective lens 18 in areas, with the result that the mentioned angle is equal to the angle $\alpha$ between the optical axis OA and the longitudinal axis LA.

The first bearing surface 42 in addition comprises a partial area 46 which is inclined to a greater extent relative to the longitudinal axis LA than the remaining section of the first bearing surface 42. This means that the angle which the surface of the partial area 46 forms with the longitudinal axis LA is greater than the area of the first bearing surface 42 which lies opposite the second bearing surface 44. The partial area 46 is provided on both sides of the first bearing section 34 relative to the objective lens 18 and does not lie opposite the second bearing surface 44. The first bearing surface 42 and/or second bearing surface 44 can gradually change the inclination relative to the longitudinal axis LA, in particular along the circumferential direction of the shaft 14. The angle of inclination of the corresponding bearing surface 42, 44 or of partial sections of the bearing surface 42, 44 can thus increase along the circumferential direction. In particular the increase can take place in the direction away from the web 38.

As is represented in particular in FIG. 6B, a different deflection of the fibre-optic light guides 31 off the longitudinal axis LA is thereby achieved. As is represented by way of example in FIG. 6B with reference to three fibre-optic light guides 31, the light cones K1, K2 and K3 generated by the fibre-optic light guides 31 and thus the corresponding main beam directions each have a different direction, i.e. the angle of the main beam direction relative to the longitudinal axis LA is different for each of the three fibre-optic light guides 31. This means that all of the fibre-optic light guides 31 are not positioned identically relative to the optical axis OA. The surface of the object illuminated by the fibre-optic light guides 31 thus does not form a ring or crown around the optical axis OA. Rather, the field of view SF, and thus the object, is illuminated homogeneously. In the schematic representation in FIG. 6B, for example, the light cones K2 and K3 overlap. In particular a very homogeneous illumination is possible even in the case of a large field of view SF of the endoscope 10.

The connecting element 38 in the embodiment shown is formed as a web, from which the first bearing surface 42 and the second bearing surface 44 protrude. The connecting element 38 serves to durably connect the second bearing section 36 to the first bearing section 34. The inner tube head 32 can thus be formed as a one-piece unit.

The inner tube head 32 can be formed symmetrical. For example, the axis of symmetry, in top view onto the distal end 16, intersects the optical axis OA and the longitudinal axis LA. If the connecting element 38 is formed as a web, the axis of symmetry can run through the web 38. The first bearing surface 42, the second bearing surface 44 and the connecting element 38, in top view onto the distal end 16, form a double T shape.

The first bearing section 34 and the second bearing section 36, as well as optionally the connecting element 38 and/or the jacket tube 26, delimit one or more chambers (e.g. chambers open on one side), in which the bundle of fibre-optic light guides 31 can be arranged. In the embodiment shown, in which the connecting element 38 is a web arranged on the axis of symmetry, two chambers are provided for the arrangement of the bundle of fibre-optic light guides 31. Each chamber therefore receives approximately half of the fibre-optic light guides 31. In the embodiment shown, each chamber is delimited by the jacket tube 26, the first bearing section 34, the connecting element 38 and the second bearing section 36.

The production of the endoscope 10 in one example embodiment is as follows:

The inner tube head 32 and the jacket tube 26, as they are represented in FIGS. 1-7, show their design in the finished endoscope 10. Prior to completion, the inner tube head 32 comprises a protrusion 48 and the jacket tube 26 comprises a recess 50. The protrusion 48 can be provided on the second bearing section 36; however, it is also possible for the protrusion 48 to be arranged on the first bearing section 34. The protrusion 48 protrudes in the direction of the longitudinal axis LA and perpendicularly to the longitudinal axis LA from the inner tube head 32, in particular from the second bearing section 36. The protrusion 48 juts out perpendicularly to the longitudinal axis LA only in the area in which it protrudes from the inner tube head 32 in the direction of the longitudinal axis LA, in particular the optical axis OA. The protrusion 48 is therefore designed as if it were applied to the second bearing section 36.

To produce the endoscope 10 the inner tube 28 is provided with the inner tube head 32, for example by connecting the inner tube head 32 to the inner tube 28. The objective lens 18 is then mounted on the inner tube head 32. After that, the bundle of fibre-optic light guides 31 is provided on the first bearing section 34 and the second bearing section 36. In particular the bundle of fibre-optic light guides 31 is clamped between the first bearing surface 42 and the second bearing surface 44. Because the first bearing surface 42 and the second bearing surface 44 are inclined relative to the longitudinal axis LA, a distal end 16 of the bundle of fibre-optic light guides 31 is bent out relative to the longitudinal axis LA.

After that, the inner tube 28, with the inner head 32 as well as the bundle of fibre-optic light guides 31, is inserted into the jacket tube 26. Because the bundle of fibre-optic light guides 31 is clamped between the first bearing section 34 and the second bearing section 36, this is achieved in a particularly simple way. Apart from the distal end 16, the bundle of fibre-optic light guides 31 runs parallel to the longitudinal axis LA; at the distal end 16 the bundle of fibre-optic light guides 31, because of the inclination of the first bearing surface 42 and the second bearing surface 44, is inclined relative to the longitudinal axis LA. The inclination relative to the longitudinal axis L is different as the partial area 46 has a different inclination relative to the longitudinal axis LA from the rest of the first bearing surface 42.

During the insertion of the inner tube 28, care is taken that the protrusion 48 is inserted into the recess 50. In this way it is achieved that the inner tube head 32, and thus its deflection relative to the longitudinal axis LA, is arranged such that the inclination of the inner tube head 32 matches the inclination of the distal end 16 of the jacket tube 26.

After that, the bundle of fibre-optic light guides 31 is secured in the inner tube head 32 and the jacket tube 26. This is achieved, for example, by connecting the named parts to each other by means of adhesive. In this way, the distal end 16 is also sealed. The distal end 16 is then ground, namely in a plane perpendicular to the optical axis OA of the objective lens 18. The distal end 16 is ground until the protrusion 48 along the longitudinal axis LA, in particular the optical axis OA of the objective lens 18, no longer juts out from the inner tube head 32. The protrusion 48 has thus been ground off flush with the inner tube head 32, in particular with the second bearing section 36.

Due to this grinding the protrusion 48 has completely vanished, i.e. it also no longer juts out perpendicularly to the longitudinal axis LA as it also juts out perpendicularly to the longitudinal axis LA only in the area in which it protrudes in the direction of the longitudinal axis LA, in particular the optical axis OA. At the same time the jacket tube 26 was also ground at the distal end 16 in such a way that the recess 50 has vanished. The structure of the distal end 16 of the endoscope 10 shown in FIGS. 1-7 thus results.

Due to the inclination of the first bearing surface 42 and/or the second bearing surface 44 relative to the longitudinal axis LA, the object to be observed with the endoscope 10 can be illuminated. The illumination is, in particular, parallel to the optical axis OA, with the result that the main intensity of the radiation emitted by the bundle of fibre-optic light guides 31 actually strikes the object to be observed by the endoscope 10. The provision of the partial area 46 which has a greater inclination relative to the longitudinal axis LA than the rest of the first bearing surface 42 helps to also illuminate the sides of the object which face away from the second bearing surface 44, i.e. in which no fibre-optic light guides 31 are arranged. In this way, the field of view of the endoscope 10, which is defined by the angle $\alpha$ of the optical axis OA and the opening angle about the optical axis OA, can be illuminated uniformly as the individual fibre-optic light guides 31 point in different directions at the distal end 16.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An endoscope, comprising:
   a main unit; and
   a shaft, the shaft being connected to the main unit, which extends along a longitudinal axis,
   wherein the shaft comprises a jacket tube, an inner tube arranged in the jacket tube for receiving an objective lens, and a bundle of fibre-optic light guides which run along the longitudinal axis in the shaft between the jacket tube and the inner tube,
   wherein at a distal end facing away from the main unit the inner tube comprises an inner tube head, which comprises a first bearing section and a second bearing section, which is connected to the first bearing section by a connecting element,
   wherein the first bearing section comprises a first bearing surface, against which the bundle of fibre-optic light guides abuts, and the second bearing section comprises a second bearing surface, against which the bundle of fibre-optic light guides abuts and which lies opposite the first bearing surface at least in areas,
   wherein, to align the bundle of fibre-optic light guides off the longitudinal axis at the distal end, an area of at least one of the first bearing surface and an area of the second bearing surface run non-parallel to the longitudinal axis,
   wherein the connecting element is formed as a web, and wherein at least one of the first bearing surface and the second bearing surface protrude from the web,
   wherein the bundle of fibre-optic light guides is separated by the connecting element into at least two partial bundles at the distal end, and
   wherein the first bearing section, the connecting element and the second bearing section, in top view onto the distal end, form a double T shape.

2. The endoscope according to claim 1, wherein at least one of the first bearing section and the second bearing section abut against an inner surface of the jacket tube.

3. The endoscope according to claim 1, wherein an objective lens, which has an optical axis which forms an angle with the longitudinal axis which is equal to an angle which the longitudinal axis, forms with the area of at least one of the first bearing surface and the area of the second bearing surface.

4. The endoscope according to claim 1, wherein partial areas of at least one of the first bearing surface and the second bearing surface are inclined to different extents relative to the longitudinal axis, wherein the angle of inclination of the partial areas increases along a circumferential direction.

5. The endoscope according to claim 1, wherein the areas of the first bearing surface and of the second bearing surface, which lie opposite each other, are inclined relative to the longitudinal axis such that the distance between them decreases in the direction towards the distal end.

6. The endoscope according to claim 1, wherein the inner tube head, in top view onto the distal end, is symmetrical relative to an axis of symmetry running through the connecting element.

7. The endoscope according to claim 1, wherein the first bearing surface and the second bearing surface, together with the connecting element, in top view onto the distal end, form one or more laterally open receiver areas for the fibre-optic light guides.

8. The endoscope according to claim 1, wherein the inner tube and the inner tube head are separate pieces connected to each other, and wherein the inner tube and the inner tube head are connected to each other by welding or soldering.

9. The endoscope according to claim 1, wherein a space delimited by the first and second bearing sections becomes smaller in the direction towards the distal end.

10. A method of securing at least one bundle of fibre-optic light guides in a shaft of an endoscope, the method comprising:
    providing a jacket tube which extends along a longitudinal axis;
    providing an inner tube, wherein at a distal end the inner tube comprises an inner tube head with a first bearing section and a second bearing section, which is connected to the first bearing section by a connecting element, wherein the first bearing section comprises a first bearing surface and the second bearing section comprises a second bearing surface, which lies opposite the first bearing surface at least in areas, and wherein at least one of an area of the first bearing surface and an area of the second bearing surface run non-parallel to the longitudinal axis, wherein first bearing section, the connecting element and the second bearing section, in top view onto the distal end, form a double T shape;
    aligning the bundle of fibre-optic light guides off the longitudinal axis at the distal end by placing the bundle of fibre-optic light guides against the first bearing surface and the second bearing surface;
    inserting the bundle of fibre-optic light guides and the inner tube into the jacket tube; and
    securing the bundle of fibre-optic light guides on at least one of the inner tube head and the jacket tube.

11. The method according to claim 10, wherein the inner tube head comprises a protrusion which protrudes in the direction of the longitudinal axis as well as perpendicularly to the longitudinal axis, and wherein the insertion of the bundle of fibre-optic light guides and the inner tube into the jacket tube is effected such that the protrusion is arranged in a recess at the distal end of the jacket tube.

12. The method according to claim 11, wherein the distal end is ground such that the extent of the protrusion is removed in the direction of the longitudinal axis.

* * * * *